United States Patent [19]

Jouffret

[11] 4,028,420

[45] June 7, 1977

[54] PROCESS FOR THE PREPARATION OF HEX-2-ENAL

[75] Inventor: Michel Jouffret, Rhone, France

[73] Assignee: Rhone-Poulenc Industries, Paris, France

[22] Filed: June 5, 1975

[21] Appl. No.: 584,118

[30] Foreign Application Priority Data

June 6, 1974 France .............................. 74.19550

[52] U.S. Cl. ........................ 260/601 R; 260/610 B
[51] Int. Cl.² ........................................ C07C 47/20
[58] Field of Search ........ 260/601 R, 610 B, 621 C

[56] References Cited

UNITED STATES PATENTS

| 2,694,090 | 11/1954 | Wild | 260/601 R |
| 3,497,561 | 2/1970 | Gelbein | 260/601 R |
| 3,839,457 | 10/1974 | Joufrett | 260/601 R |

OTHER PUBLICATIONS

Swern, Organic Peroxides, vol. II, pp. 157–159.
Farkas et al., "J.A.C.S." vol. 72, (1933), pp. 3333–3337.
Tobolsky, Organic Peroxides, pp. 117–119.

Primary Examiner—James O. Thomas, Jr.
Assistant Examiner—W. B. Lone
Attorney, Agent, or Firm—Stevens, Davis, Miller & Mosher

[57] ABSTRACT

The rate of palladium catalyzed deperoxidation of cyclohexyl hydroperoxide to form hex-2-enal is increased by carrying out the deperoxidation using an aqueous solution containing both a palladium derivative and a derivative of divalent iron.

9 Claims, No Drawings

PROCESS FOR THE PREPARATION OF HEX-2-ENAL

This invention relates to the preparation of hex-2-enal.

U.S. Pat. No. 3,839,457 describes a process for the preparation of hex-2-enal by subjecting cyclohexyl hydroperoxide in the liquid phase to the action of an aqueous solution of a palladium derivative.

This publication also indicates that it is possible to carry out the process in the presence of an organic solvent for the hydroperoxide, the organic solvent preferably being immiscible with water.

Cyclohexyl hydroperoxide can be prepared from cyclohexanol or by oxidation of cyclohexane in the liquid phase, without a catalyst, using a molecular oxygen containing gas, optionally in the presence of agents which can complex the metal ions. Processes of this type are described for example in French Pat. Nos. 1,404,723 and 1,491,518. The hydroperoxide can be purified by known methods such as conversion to the sodium salt and treatment with carbon dioxide.

The palladium derivatives used as the catalyst in the decomposition of the hydroperoxide can be a palladium halide such as, for example, a chlorinated derivative. The amount of catalyst is generally chosen so as to provide 1 to 20 gram atoms of elementary metal per 100 mols of hydroperoxide.

The organic solvents which can be used in the decomposition of the hydroperoxide can be a linear ether; an ester such as a lower alkyl alkyl- or aryl-carboxylate; or a hydrocarbon such as an alkane or alkene with 6 to 20 carbon atoms, a cycloalkane or cycloalkene with 5 to 16 carbon atoms in the ring, optionally substituted by one or more alkyl radicals with 1 to 4 carbon atoms; benzene or its derivatives which are mono-substituted or poly-substituted by chlorine or fluorine, or an alkyl radical with 1 to 4 carbon atoms or a group such as an alkoxy group with 1 to 4 carbon atoms, a cyano group or a nitro group, or a phenyl radical derived from one of the substituted derivatives of benzene described above.

The publication mentioned above indicates that the amounts of water and, where appropriate, of organic solvent employed in the decomposition of the hydroperoxide are such that the proportion by weight of hydroperoxide in the reaction mixture is between 2% and 50%, and preferably between 5 and 30%. When an organic solvent is used, the weight of water is at least of the order of 1% relative to the weight of the organic solution.

This palladium catalysed process gives good yields, but requires relatively long reaction times in order to achieve a high degree of decomposition of the hydroperoxide; its use thus leads to relatively low productivity of the deperoxidation plant. It was therefore desirable to have available a process for the preparation of hex-2-enal which overcomes this low productivity problem whilst retaining the advantages, particularly the good yields, of the palladium catalysed process described above.

The present invention provides a process for the preparation of hex-2-enal which comprises subjecting cyclohexyl hydroperoxide in the liquid phase to the action of an aqueous solution containing both a palladium derivative and a catalytic amount of a derivative of divalent iron. The deperoxidation may optionally be carried out in the presence of an organic solvent for the hydroperoxide, the organic solvent being one which is immiscible with water.

The use of an aqueous solution containing both a palladium derivative and a derivative of iron-II, in solution, in suitable proportions, makes it possible to increase considerably the rate of reaction to the extent of reducing, by more than half, the period of time necessary for complete decomposition of cyclohexyl hydroperoxide to form hex-2-enal.

The derivatives of iron-II used in the invention are those which are soluble in or which have been rendered soluble in water under the reaction conditions. The radical associated with the iron is not critical insofar as it fulfills these solubility conditions. Salts of inorganic acids, and especially ferrous sulphate, ferrous nitrate of ferrous chloride, are generally used. Ferrous chloride tetrahydrate is preferably used to form the aqueous solution used in the process according to the invention.

The amount of the derivative or iron-II used, expressed as the number of gram atoms of elementary metal per 100 mols of hydroperoxide is not critical and normally can be between 0.01 and 20; more precisely, this amount is chosen within the above-mentioned range so that it provides the reaction medium with a number of gram atoms of elementary iron which is at most equal to the number of gram atoms of palladium.

The palladium derivative used in the invention can be any one of those used in the process described in the above-mentioned Patent Specification, e.g. halogenated derivatives of palladium such as alkali metal or alkaline earth metal halogenopalladates which are soluble in water, and particularly alkali metal chloropalladates such as sodium chloropalladate.

The general working conditions of the present process are apart from the use of the ferrous derivative, substantially the same as those used in the process described in the abovementioned Patent Specification and reference should be made to the above-mentioned Patent Specification for further details of the general working conditions. From the practical point of view, cyclohexyl hydroperoxide can be introduced, in the pure state, into the aqueous solution of the metal derivatives at a temperature from 50° C., up to the boiling point of the mixture; if it has been decided to use an organic solvent, this can be added to the aqueous solution employed.

However, it is also possible, for safety reasons, to use the hydroperoxide in the form of a solution in the organic solvent chosen. For example, it is convenient to use the hydroperoxide in solution in the corresponding hydrocarbon from which it was derived by oxidation, that is to say cyclohexane; it is particularly advantageous to use directly the crude solution resulting from the oxidation process, which contains the hydroperoxide, after this solution has been preconcentrated and washed with water.

In an alternative procedure, the aqueous phase containing the metal catalysts can be introduced into a solution of cyclohexyl hydroperoxide in cyclohexane, heated beforehand to between 50° C., and the boiling point of the mixture.

Whatever procedure is chosen, the reaction is generally carried out by bringing the pH of the aqueous phase to a value of between 0 and 4, and preferably of approximately 1, by adding a strong acid.

When the introduction of the reagents is complete, the reaction mixture is kept at the desired temperature until the hydroperoxide employed has been completely decomposed. The hex-2-enal can then be recovered from the reaction mixture by procedures substantially similar to those described in the above-mentioned Patent Specification and once again, reference should be made to the Patent Specification for full details.

The following Examples are given to illustrate the invention.

EXAMPLES 1 to 3

These three Examples are carried out using a purified cyclohexyl hydroperoxide, containing 94.6% by weight of pure hydroperoxide, and varying the amount of metal catalysts.

The common procedure is as follows:

An aqueous solution containing the amounts of sodium chloropalladate ($Na_2PdCl_4$) and ferrous chloride tetrahydrate ($FeCl_2.4H_2O$) specified below, is brought to a pH of approximately 1 by addition of a small amount of hydrochloric acid. The acidified catalyst solution and cyclohexane is then introduced into a 2 liter glass reactor equipped with a central stirrer, a reflux condenser, a dropping funnel and a thermometer. This mixture is heated to the desired temperature, generally its characteristic boiling point, and the purified cyclohexyl hydroperoxide is then added as rapidly as possible to the mixture which is stirred at the chosen temperature for the specified period of time, until the peroxidic oxygen has completely disappeared.

At the end of this period of time, the reaction mixture is cooled, filtered and thereafter decanted. The aqueous phase is extracted with diethyl ether. The combined organic phases are distilled and the ether and part of the cyclohexane are removed during this process. The balance of the reaction, that is to say the yields, relative to the pure cyclohexyl hydroperoxide introduced, of hex-2-enal, cyclohexanol and cyclohexanone formed is determined by vapour phase chromatographic analysis.

Two comparison experiments were carried out using only sodium chloropalladate as the catalyst. (Experiments A and B).

The various results are given in the Table which follows.

1,585,374, are introduced into a glass reactor equipped as described in the preceding Examples.

The cyclohexane oxidation product contains 40 g. (0.345 mol) of pure cyclohexyl hydroperoxide in addition to other products such as cyclohexanol (13.3 g.) and cyclohexanone (6.73 g.); the remainder consists mainly of cyclohexane.

This mixture is heated to a temperature of about 73° C. An aqueous solution of metal salts, which was prepared by dissolving 5 g. (0.0164 gram atom of palladium) of $Na_2PdCl_4$ and 0.34 g. (0.0017 gram atom of iron) of $FeCl_2.4H_2O$ in 30 g. of water and which was brought to pH=1 by means of hydrochloric acid, is then introduced as rapidly as possible into the above mixture.

Deperoxidation is complete in 1 hour, and vapour phase chromatographic analysis of the residue obtained at the end of the treatment shows that it consists of hex-2-enal, cyclohexanol and cyclohexanone in respective yields, relative to the pure hydroperoxide used in the reaction, of 44.8%, 20.6% and 19.5%.

I claim:

1. In a process for preparing hex-2-enal by subjecting cyclohexyl hydroperoxide is the liquid phase to the action of an aqueous solution of an alkali metal or alkaline earth metal halogenopalladate which is soluble in water, at a temperature from 50° C. up to the boiling point of the mixture, the improvement wherein the aqueous phase also contains a divalent iron salt of an inorganic acid in an amount so as to provide 0.01 to 20 gram atoms of elementary iron per 100 mols of hydroperoxide, and a number of gram atoms of iron which is at most equal to the number of gram atoms of palladium.

2. A process according to claim 1, wherein the divalent iron salt is ferrous sulphate, ferrous nitrate or ferrous chloride.

3. A process according to claim 2, wherein the divalent iron salt is ferrous chloride tetrahydrate.

4. A process according to claim 1, wherein prior to subjecting the cyclohexyl hydroperoxide to the action of the aqueous solution, the pH of the aqueous solution is brought to a value of 0 to 4 by addition of a strong acid to the solution.

| EXAMPLES/EXPERIMENTS | 1 | 2 | 3 | A | B |
| --- | --- | --- | --- | --- | --- |
| 94.6% pure cyclohexyl hydroperoxide grams; mols | 42.28; 0.345 | 42.17 ; 0.344 | 42.31 ; 0.345 | 42.16 ; 0.344 | 42.19 ; 0.344 |
| Catalysts*; grams | $Na_2PdCl_4$ :10  $FeCl_2.4H_2O$:0.34 | $Na_2PdCl_4$ :5  $FeCl_2.4H_2O$:0.34 | $Na_2PdCl_4$ :5  $FeCl_2.4H_2O$:3.4 | $Na_2PdCl_4$:10 | $Na_2PdCl_4$:5 |
| [Pd]gram atoms/100 mols of hydroperoxide | 10 | 5 | 5 | 10 | 5 |
| [Fe]gram atoms/100 mols of hydroperoxide | 0.5 | 0.5 | 5 | 0 | 0 |
| $H_2O$ ; grams | 30 | 30 | 30 | 30 | 30 |
| Cyclohexane ; grams | 234 | 234 | 234 | 234 | 234 |
| Temperature | 73° C. | 73° C. | 73° C. | 73° C. | 73° C. |
| Duration | 45 mins. | 60 mins. | 15 mins. | 2 hrs. 30 mins. | 6 hrs. |
| Yield of hex-2-enal | 55.5% | 55.7% | 47% | 53.7% | 48.4% |
| Yield of cyclohexanol | 4.4% | 7.9% | 5.1% | 0.7% | 10.9% |
| Yield of cyclohexanone | 11.7% | 15.5% | 15.7% | 16.7% | 16.9% |

*The sodium halogenopalladate used in these examples is the product supplied by Messrs. PROLABO under the name of palladium (palladous) chloride, containing 35% by weight of elementary palladium.

EXAMPLE 4

279 g. of a crude cyclohexane oxidation product which was prepared by the process described in French Patent Specification No. 1,491,518 and which was preconcentrated and washed with water by the process described in French Patent Specification No.

5. A process according to claim 4, wherein the pH is approximately 1.

6. A process according to claim 1, wherein the cyclohexyl hydroperoxide is subjected to the action of the aqueous solution in the presence of an organic solvent for the hydroperoxide, the organic solvent being one which is immiscible with water.

7. A process according to claim 6, wherein the organic solvent is cyclohexane.

8. A process according to claim 7, wherein a cyclohexane oxidation product, obtained by oxidising cyclohexane with molecular oxygen in the liquid phase in the absence of a catalyst, is subjected to the action of the aqueous solution.

9. A process according to claim 8, wherein the cyclohexane oxidation product has been concentrated to increase the cyclohexyl hydroperoxide concentration and washed with water, before being subjected to the action of the aqueous solution.

* * * * *